(12) United States Patent
Powis et al.

(10) Patent No.: US 7,081,475 B2
(45) Date of Patent: Jul. 25, 2006

(54) WORTMANNIN ANALOGS AND METHODS OF USING SAME

(75) Inventors: Garth Powis, Tucson, AZ (US); Wipf Peter, Pittsburgh, PA (US)

(73) Assignees: Prolx Pharmaceuticals Corp., Tuscon, AZ (US); Arizona Board of Regents, Acting on behalf of the University of Arizona, Tuscon, AZ (US); University of Pittsburgh, Pittsburgh, PA (US)

( * ) Notice: Subject to any disclaimer, the term of this patent is extended or adjusted under 35 U.S.C. 154(b) by 170 days.

(21) Appl. No.: 10/245,779

(22) Filed: Sep. 16, 2002

(65) Prior Publication Data

US 2003/0109572 A1 Jun. 12, 2003

Related U.S. Application Data

(60) Provisional application No. 60/322,139, filed on Sep. 14, 2001.

(51) Int. Cl.
*A61K 31/352* (2006.01)
*C07D 311/94* (2006.01)

(52) U.S. Cl. ...................................... 514/453; 549/276
(58) Field of Classification Search ................ 549/276; 514/453
See application file for complete search history.

(56) References Cited

U.S. PATENT DOCUMENTS 6,703,414 B1 * 3/2004 Powis et al. ................ 514/422

FOREIGN PATENT DOCUMENTS

GB 2302021 1/1997
WO WO 03/024183 * 3/2003

OTHER PUBLICATIONS

Helveita Chimica Acta—vol. 58, Fasc. 6 (1975)—Nr. 179-180, "Selektive Funktionalisierung von Wortmannin mit Hilfe einer Furanring-Maskierung", von Walkter Haefliger, Zoltan Kis und Daniel Hauser, Sandoz AG, Pharma Department, Chemische Forschung, CH-4002 Basel, pp. 1620-1628.

Norman, Bryan H. et al., *Studies on the Mechanism of Phosphatidylinositol 3-Kinase Inhibition by Wortmannin and Related Analogs*, J. Med. Chem., 1996, 39:1106-1111.

* cited by examiner

*Primary Examiner*—Kamal A. Saeed
*Assistant Examiner*—Rebecca Anderson
(74) *Attorney, Agent, or Firm*—Pepper Hamilton LLP

(57) ABSTRACT

Novel Wortmannin analogs and their use in inhibiting inhibiting PI-3-kinase activity in mammals as well as tumor formation in a subject are described herein.

4 Claims, 9 Drawing Sheets

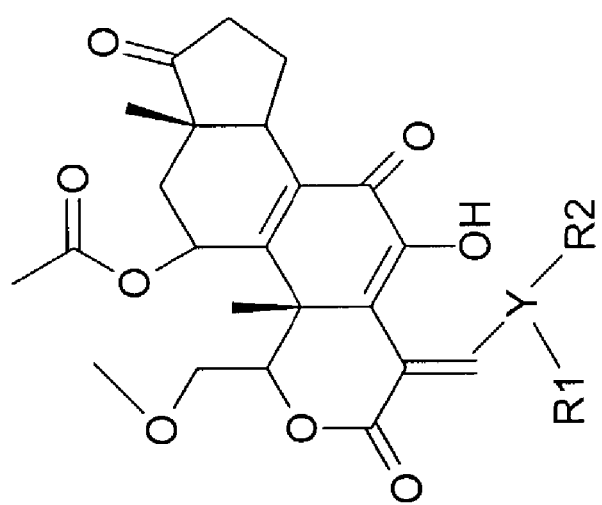
or
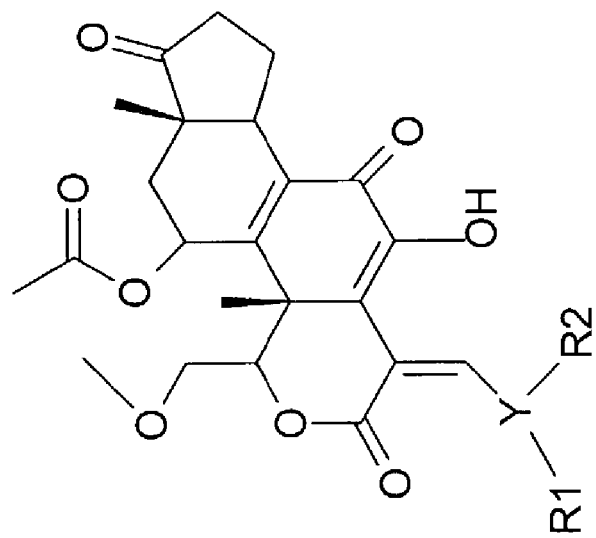
FIG. 1

DJM2-166
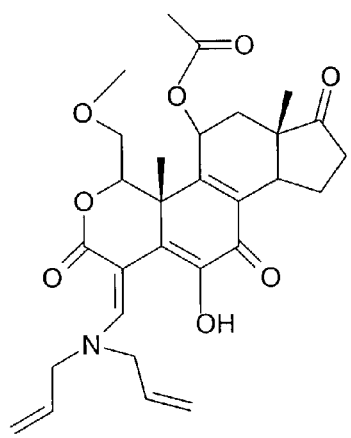 or 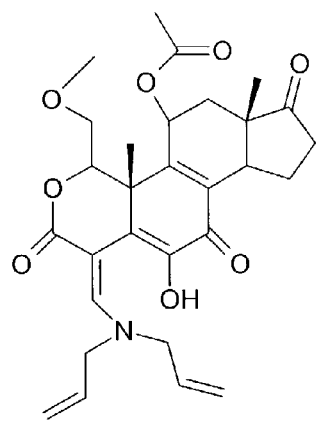
DJM2-167
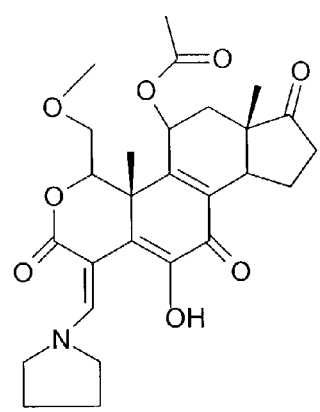 or 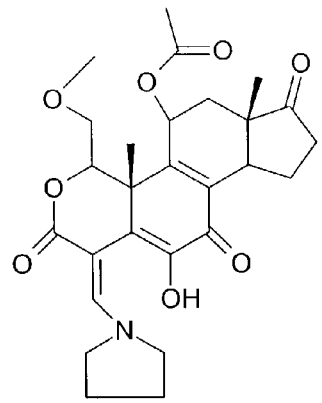
DJM2-181
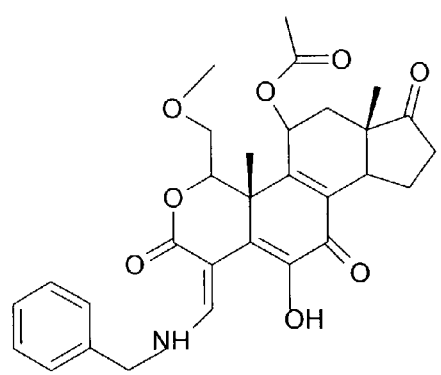 or 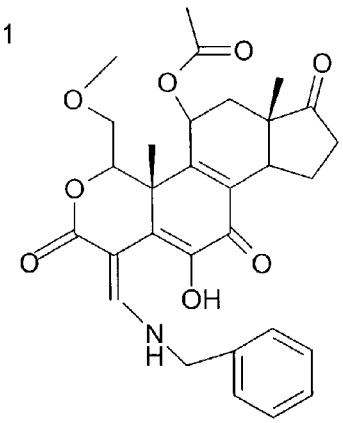
FIG. 2

FIG. 9

WORTMANNIN ANALOGS AND METHODS OF USING SAME

CROSS-REFERENCE TO RELATED APPLICATIONS

This application claims priority to U.S. Provisional Application No. 60/322,139 filed Sep. 14, 2001, which is hereby incorporated by reference in its entirety herein.

The United States Government may have certain interests to this application as a Federal Research Sponsor under NIH/NIG Grant No. U01 CA 052995.

BACKGROUND OF THE INVENTION

The present invention relates to Wortmannin analogs, and has application to methods of using these derivatives to inhibit PI-3-kinase activity and to treat certain malignant tumors. Wortmannin is a known potent inhibitor of phosphotidylinositol-3-kinase (PI-3-kinase) and anti-cancer agent. Wortmannin is a naturally occurring compound isolated from culture broths of the fungus Penicillium wortmannin and has the basic structure shown in U.S. Pat. No. 5,480,906, which is incorporated herein by reference.

One of the disadvantages of wortmannin is its toxicity to living creatures. Even in low dosages, wortmannin in pure form was often lethal to laboratory animals.

SUMMARY OF THE INVENTION

The invention provides novel wortmannin analogs as well as method of inhibiting cancer in a subject comprising administering to a subject a pharmaceutically effective dose of a compound selected from the group of consisting of those wortmannin analogs described in FIGS. 1–3.

The present invention also provides for a method of inhibiting PI-3-kinase activity in mammals by administration of an effective amount of one of the compounds of this invention. Since PI-3-kinase activity is a factor in certain types of cancer, the invention also provides for use of the compounds as anti-cancer (anti-tumor) agents, and also for pharmaceutical formulations that includes the compound in combination with a pharmaceutically acceptable carrier, recipient or diluent.

The present invention also provides for a method of inhibiting PI-3-kinase activity in mammals by administration of an effective amount of one of the compounds of this invention. Since PI-3-kinase activity is a factor in certain types of cancer, the invention also provides for use of the compounds as anti-cancer (anti-tumor) agents, and also for pharmaceutical formulations which includes the compound in combination with a pharmaceutically acceptable carrier, excipient or diluent.

BRIEF DESCRIPTION OF THE DRAWINGS

FIG. 1 illustrates the basic wortmannin analog structure in accordance with the present invention;

FIG. 2 illustrates the structure of certain wortmannin analog structures in accordance with the present invention;

Figure 9:
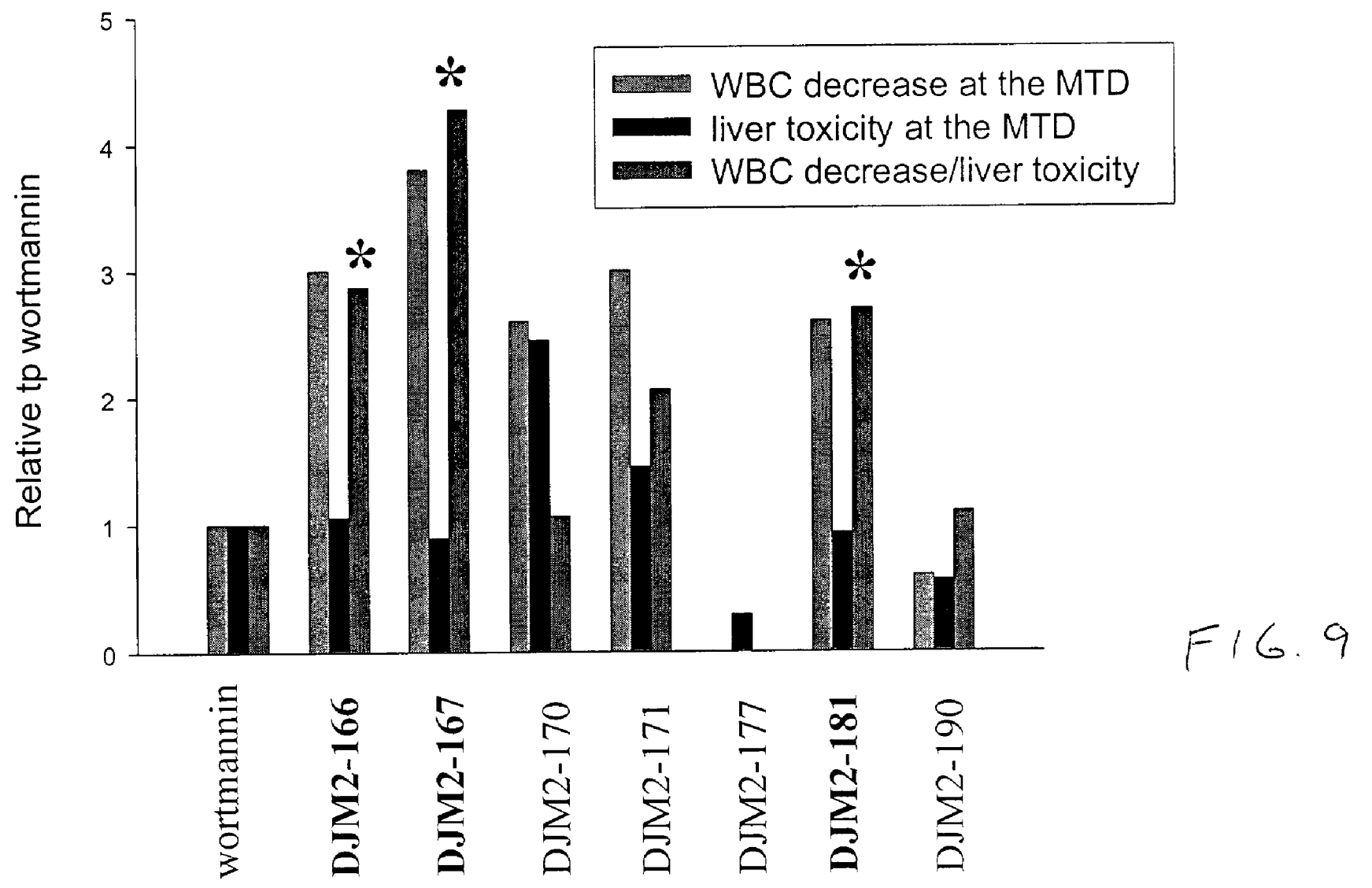

FIG. 9 is a summary of the data for Wortmannin and the Wortmannin analogs shown in FIGS. 2 & 3.

DETAILED DESCRIPTION OF THE INVENTION

Figure 3:
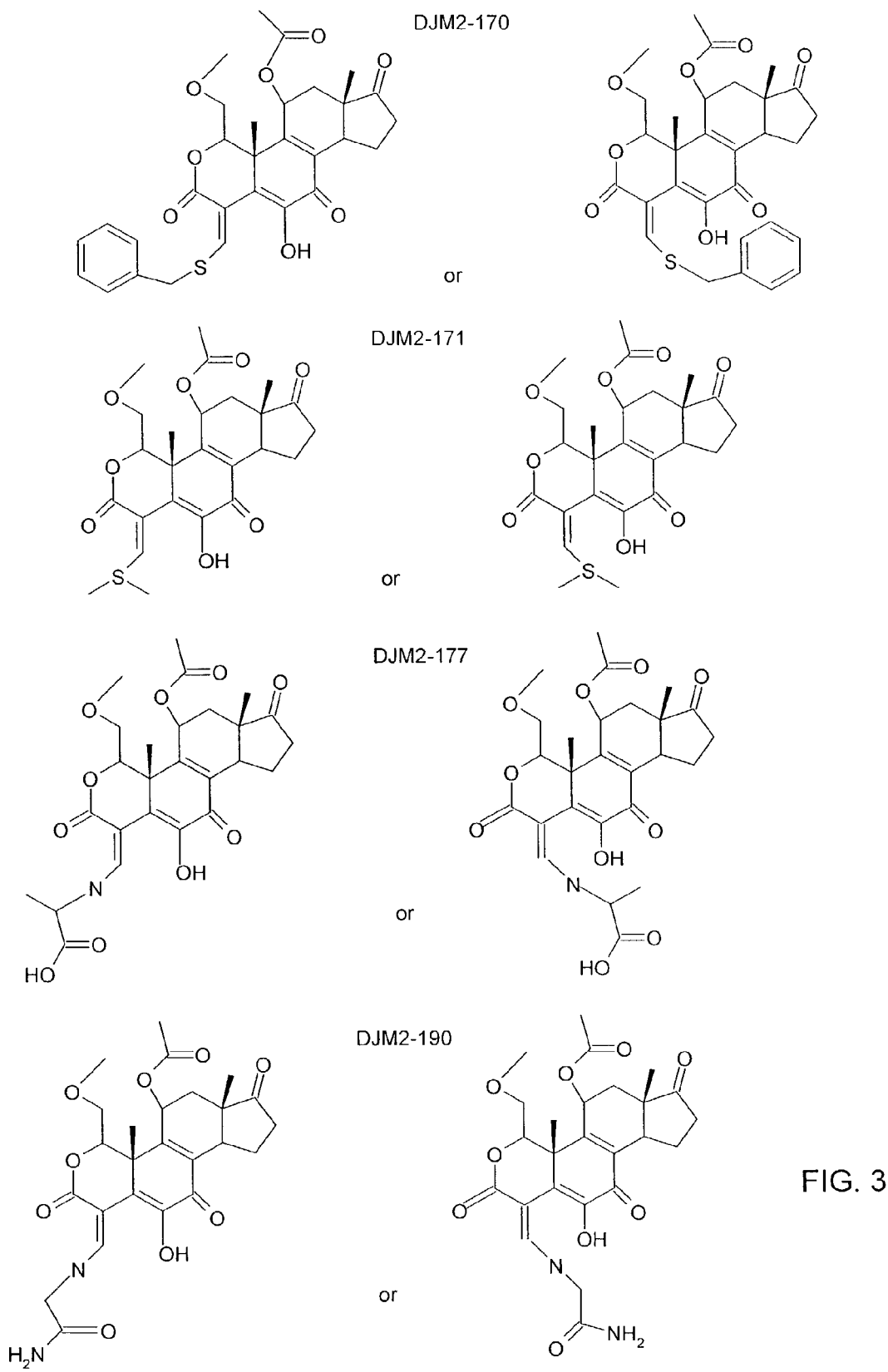
FIG. 3 illustrates the structure of certain other wortmannin analog structures in accordance with the present invention.
Figure 4:
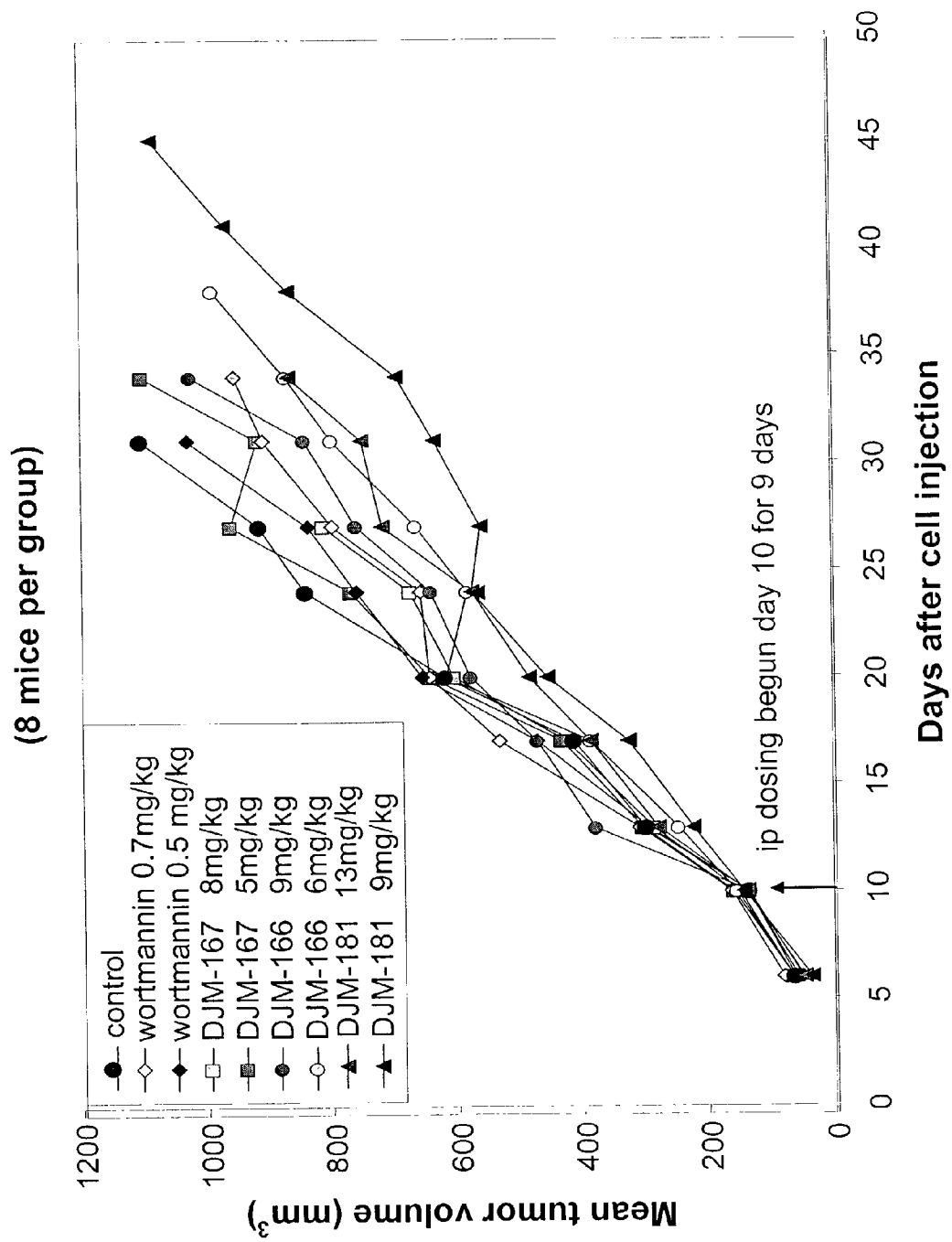
FIG. 4 illustrates the effect of Wortmannin and Analogs (See FIG. 2) Against PC-3 Human Prostate Cancer.
Figure 5:
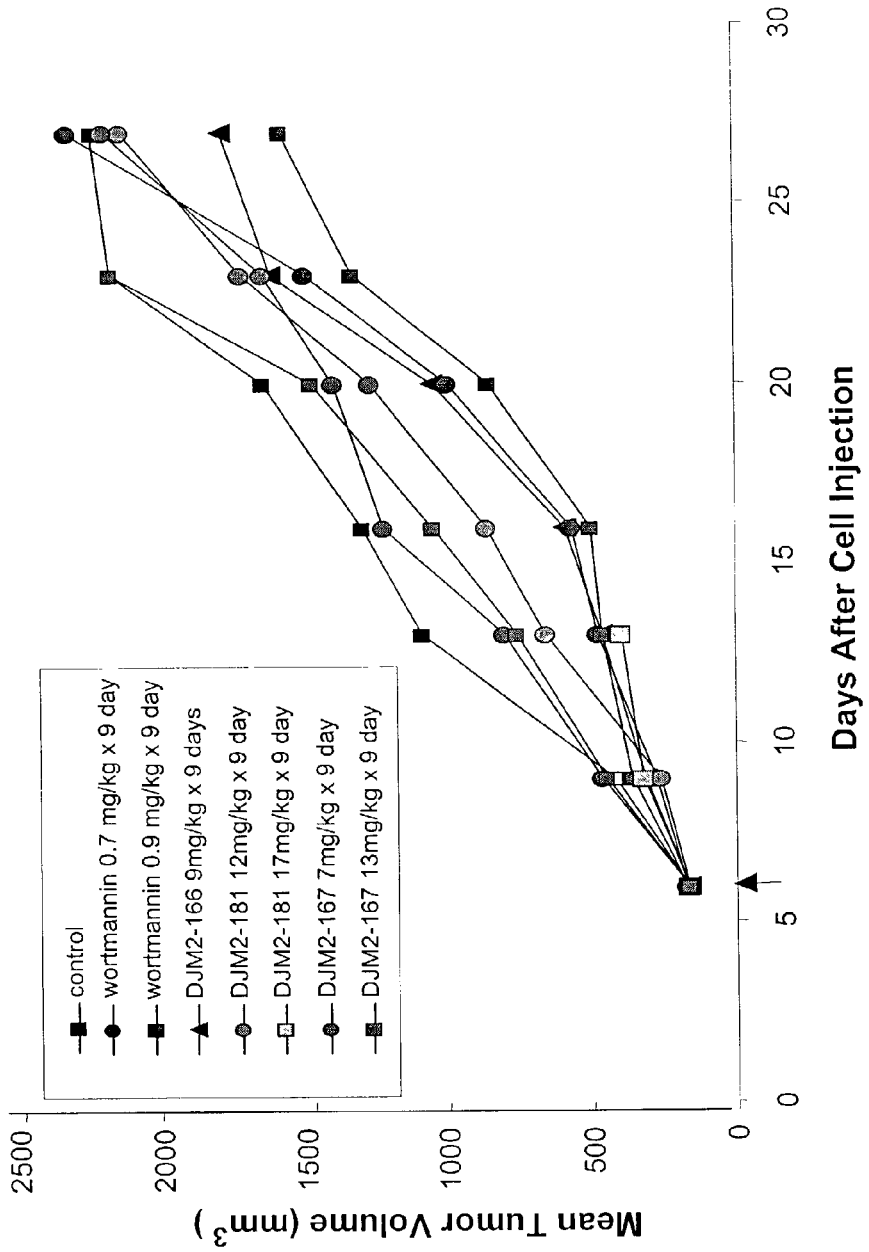
FIG. 5 illustrates the effect of Wortmannin and Analogs against HT-29 Human Colon Cancer.
Figure 6:
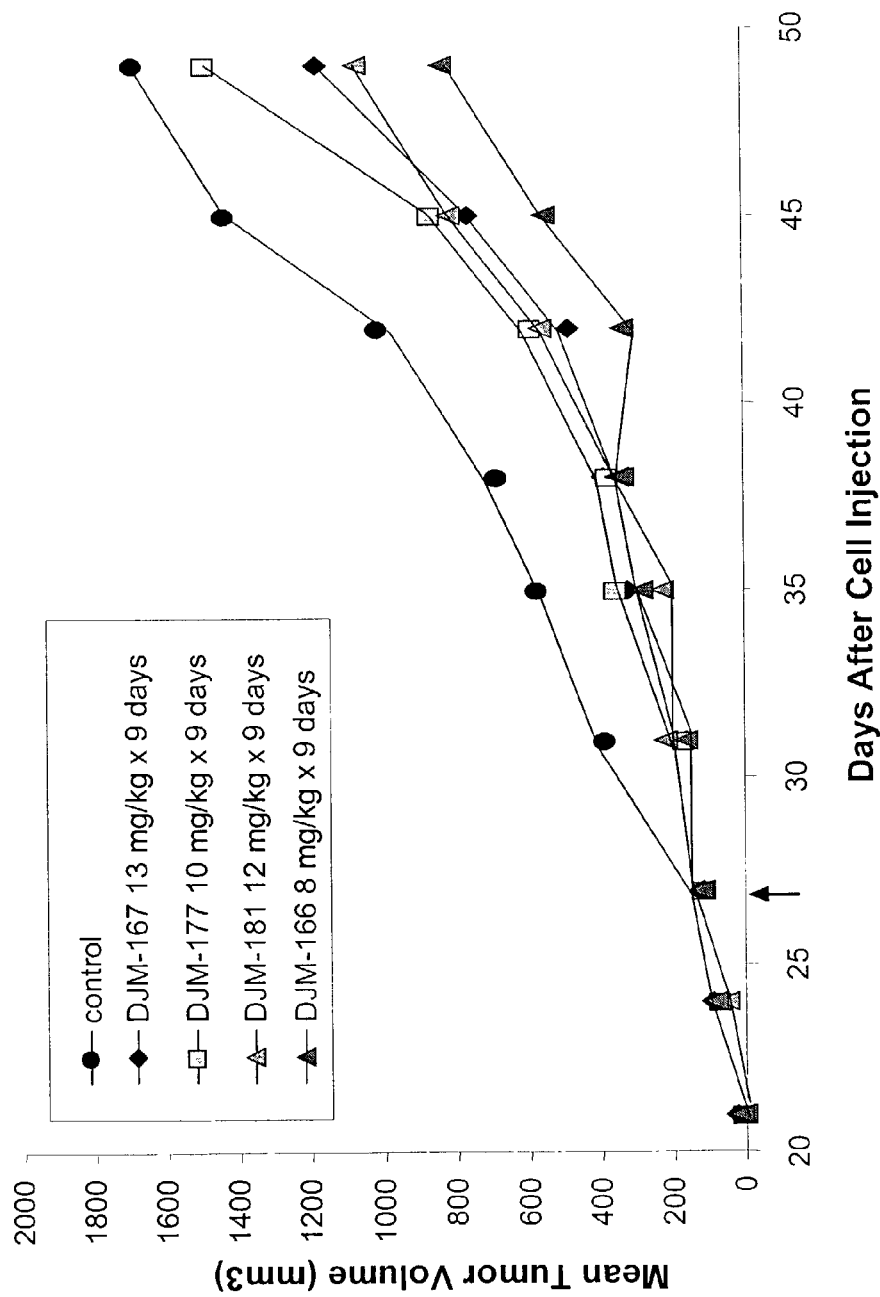
FIG. 6 illustrates the effect of Wortmannin Analogs against OVCAR-3 Human Ovarian Tumor.
Figure 7:
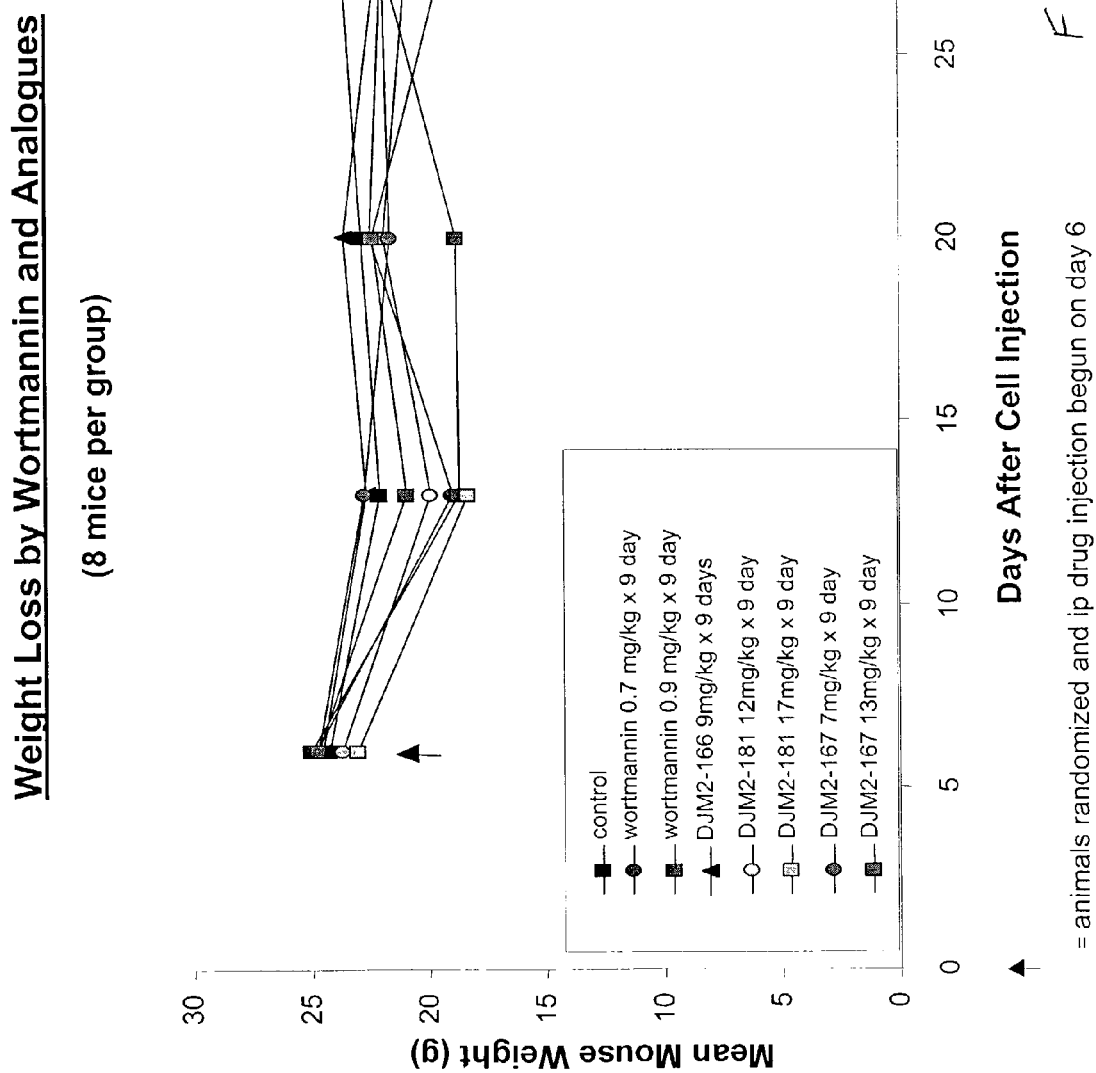
FIG. 7 illustrates the effect on Weight Loss by Wortmannin and Analogues.
Figure 8:
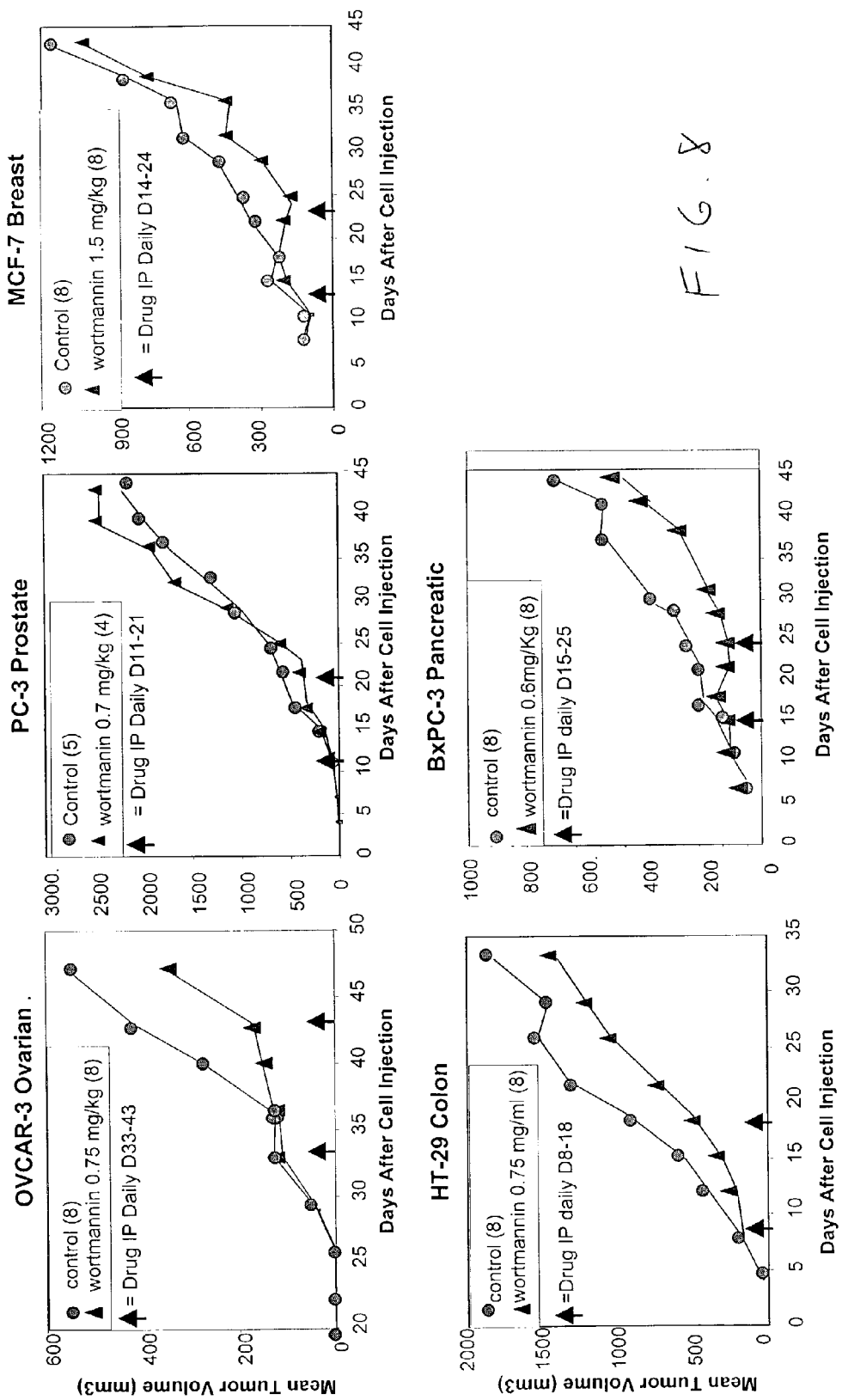
FIG. 8 illustrates the Ant tumor Activity of Wortmannin.

The current invention concerns the discovery that wortmannin analogs are useful in the inhibition of cancer. FIG. 1 illustrates the general structure of compounds in accordance with the present invention. FIG. 2 illustrate specific wortmannin analogs in accordance with the present invention and FIG. 3 illustrates certain other wortmannin analogs that may be useful in accordance with the present invention.

The biosynthetic production of wortmannin is well known in the art and the analogs are synthesized from wortmannin. U.S. Pat. No. 5,480,906, which is incorporated herein by reference in its entirety, describes typical synthetic schemes. Typically, wortmannin is produced by the fermentation of any one of a number of previously disclosed microorganisms such as Talaromyces wortmannin and Penicillium wortmannin, Myrothecium roridium, and Fusarium. Following fermentation, wortmannin is extracted and purified via known methods. Preferably, wortmannin is microbially synthesized and isolated in substantially pure form from a fermentation culture) one such fermentation culture is identified as A24603.1).

Culturing the strain under submerged aerobic conditions in a suitable culture medium until a recoverable amount of wortmannin is produced produces Wortmannin. Wortmannin can be recovered using various isolation and purification procedures understood in the art.

The medium used to grow the culture can be any one of a number of media. For economy in production, optimal yield, and ease of product isolation, however, preferred carbon sources in large-scale fermentation are glucose and soluble starch such as corn starch. Maltose, ribose, xylose, fructose, galactose, mannose, mannitol, potato dextrin, methyl oleate, oils such as soybean oil and the like can also be used.

Preferred nitrogen sources are enzyme-hydrolyzed casein and cottonseed flour, although pepsinized milk, digested soybean meal, fish meal, corn steep liquor, yeast extract, acid-hydrolyzed casein, beef extract, and the like can also be used.

Among the nutrient inorganic salts that can be incorporated in the culture media are the customary soluble salts capable of yielding calcium, magnesium, sodium, ammonium, chloride, carbonate, sulfate, nitrate, zinc, and like ions. Essential trace elements necessary for the growth and development of the organism also should be included in the culture medium. Such trace elements commonly occur as impurities in other substituents of the medium in amounts sufficient to meet the growth requirements on the organism.

For production of substantial quantities of wortmannin, submerged aerobic fermentation in stirred bioreactors is preferred. Small quantities of wortmannin may be obtained by shake-flask culture. Because of the time-lag in production commonly associated with inoculation of large bioreactors with the spore form of the organism, it is preferable to use vegetative inoculum. The vegetative inoculum is prepared by inoculating a small volume of culture medium with the spore form or mycelial fragments of the organism to obtain a fresh, actively growing culture of the organism. The vegetative inoculum medium can be the same as that used for larger fermentations, but other media are also suitable.

Following its production, wortmannin can be recovered from the fermentation medium by methods used in the art. The wortmannin produced during fermentation of the A24603.1 organism, for example, occurs mainly in the broth.

Typically, wortmannin can be recovered from the biomass by a variety of techniques. A preferred technique involves filtering whole fermentation broth with a ceramic filter. The filtrate is eluted with an organic solvent such as ethyl acetate and concentrated. The concentrate is suspended in alcohol until crystallization occurs and the solution is filtered, washed and dried. For confirmation, the crystalline material is dissolved in an organic solvent and chromatographed on a reverse-phase silica gel absorbent ($C_8$ or $C_{18}$). Fractions are eluted in an organic-aqueous buffer such as 60% acetonitrile.

Wortmannin may be further manipulated to arrive at the compounds of the present invention. Although the synthesis of particular analogs of wortmannin are illustrated below, other synthetic schemes common in the art will allow one ordinarily skilled in the art to synthesize compounds in accordance with the present invention, and the synthetic schemes set forth herein should, in no way, be considered limiting.

Acetic acid 4-diallylaminomethylene-6-hydroxy-1-α-methoxymethyl-10β,13β-dimethyl-3,7,17-trioxo-1,3,4,7,10,11β,12,13,14α,15,16,17-dodecahydro-2-oxa-cyclopenta[a]phenanthren-11-yl ester (djm2-166).

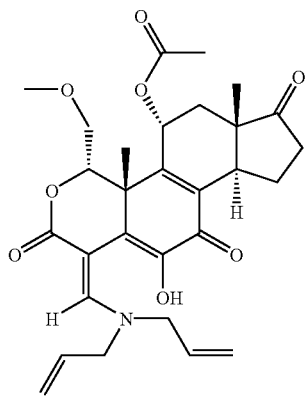

To a solution of wortmannin (10.7 mg, 25.0 μmol) in $CH_2Cl_2$ (125 μL) was added a freshly prepared 0.2 M stock solution of diallylamine (138 μL, 27.5 μmol) in $CH_2Cl_2$. The reaction mixture was stirred at room temperature for 1 h. The solvent and excess amine were removed in vacuo, and the product was purified via chromatography on $SiO_2$ (hexanes/ethyl acetate, 1:9) to give djm2-166 (9.0 mg, 17 μmol, 68%) as an orange oil: $[α]_D$ −630 (c 0.0015, $CH_2Cl_2$, 23° C.); IR (KBr) 3391, 1743, 1695, 1685, 1622, 1569, 1222, 1111, 1100 cm$^{-1}$; $^1$H NMR δ 8.20 (s, 1 H), 6.81 (s, 1 H), 6.06 (dd, 1 H, J=7.4, 4.8 Hz), 5.85 (br s, 1 H), 5.62 (br, 1 H), 5.44–5.04 (m, 4 H), 4.48 (dd, 1 H, J=7.2, 1.9 Hz), 4.05–3.60 (m, 4 H), 3.26 (s, 3 H), 3.27–3.20 (m, 1 H), 3.16 (dd, 1 H, J=10.9, 7.2 Hz), 3.00–2.90 (m, 2 H), 2.59 (dd, 1 H, J=19.4, 8.6 Hz), 2.40 (dd, 1 H, J=14,4, 7.7 Hz), 2.35–2.07 (m, 2 H), 2.07 (s, 3 H), 1.83 (dd, 1 H, J=14.4, 4.7 Hz), 1.54 (s, 3 H), 0.86 (s, 3 H); $^{13}$C NMR δ 217.0, 178.5, 169.6, 164.8, 156.3, 151.5, 139.0, 136.9, 132.2, 131.3, 127.7 (2 C), 119.2, 89.0, 81.9, 73.1, 67.6, 59.1, 50.9 (2 C), 48.9, 42.3, 42.2, 37.5, 36.0, 24.6, 22.2, 20.8, 16.1; MS (EI) m/z (rel. intensity) 525 (M$^+$, 11), 466 (17), 391 (15), 350 (14), 323 (13), 266 (17), 239 (17), 60 (100); HRMS (EI) calculated for $C_{29}H_{35}NO_8$ 525.2363. found 525.2386.

Acetic acid 6-hydroxy-1α-methoxymethyl-10β,13β-dimethyl-3,7,17-trioxo-4-pyrrolidin-1-yl-methylene-1,3,4,7,10,11β,12,13,14α,15,16,17-dodecahydro-2-oxa-cyclopenta[a]phenanthren-11-yl (djm2-167).

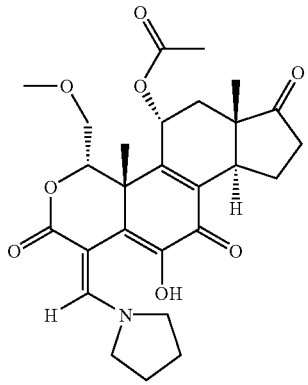

To a solution of wortmannin (30.0 mg, 70.0 μmol) in $CH_2Cl_2$ (200 μL) was added pyrrolidine (7.0 μL, 84 μmol) in $CH_2Cl_2$. The reaction mixture was stirred at room temperature for 1 h. The solvent and excess thiol were removed in vacuo and the product was purified by chromatography on $SiO_2$ (hexanes/ethyl acetate 9:1, then 1:1) to give djm2-167 (30.0 mg, 60.6 μmol, 86%) as an orange oil: $[α]_D$ −390 (c 0.0073, $CH_2Cl_2$, 23° C.); IR (KBr) 337, 1740,1684, 1617, 1570, 1261, 1221, 1099, 1018 cm$^{-1}$; $^1$H NMR δ 8.29 (s, 1 H), 6.72 (s, 1 H), 6.07 (dd, 1 H, J=6.9, 4.8 Hz), 4.47 (dd, 1 H, J=7.0, 1.9 Hz), 3.80–3.70 (m, 2 H), 3.25 (s, 3 H), 3.25–3.14 (m, 2 H), 3.02–2.90 (m, 2 H), 2.69 (br s, 1 H), 2.58 (dd, 1 H, J=19.1, 8.4 Hz), 2.39 (dd, 1 H, J=14.6, 7.8 Hz), 2.32–2.08 (m, 2 H), 2.06 (s, 3 H), 1.99–1.95 (m, 5 H), 1.84 (dd, 1 H, J=14.5, 4.2 Hz), 1.56 (s, 3 H), 0.86 (s, 3 H); $^{13}$C NMR δ 217.5, 178.9, 169.9, 164.9, 153.9, 151.3, 137.6, 137.1, 129.2, 89.4, 82.1, 73.3, 67.7, 59.3, 55.2, 49.2 (2 C), 42.6, 42.4, 37.8, 36.3, 25.6 (2 C), 24.5, 22.4, 21.0, 16.3; MS (EI) m/z (rel. intensity) 499 (M$^+$, 1), 439 (2), 365 (7), 167 (35), 149 (100); HRMS (EI) calculated for $C_{27}H_{33}NO_8$ 499.2206. found 499.2191.

Acetic acid 4-[(benzylmethylamino)methylene]-6-hydroxy-1α-methoxymethyl-10β,13β-dimethyl-3,7,17-trioxo-1,3,4,7,10,11β,12,13,14α,15,16,17-dodecahydro-2-oxa-cyclopenta[a]phenanthren-11-yl ester (djm2-181).

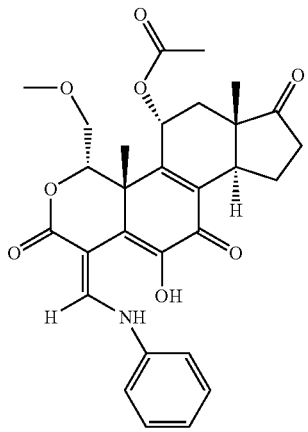

To a solution of wortmannin (10.7 mg, 25.0 μmol) in of $CH_2Cl_2$ (125 μL) was added a freshly prepared 0.2 M solution of N-methylbenzylamine (185 μL, 37.0 μmol) in $CH_2Cl_2$. The reaction mixture was stirred at room temperature for 2 h. The solvent was removed in vacuo, and the product was purified by chromatography on SiO$_2$ (hexanes/ethyl acetate, 1:9) to give djm2-181 (13.3 mg, 24.2 µmol, 97%) as an orange oil: $[\alpha]_D$ −835 (c 0.0014, CH$_2$Cl$_2$, 3° C.); IR (neat) 1742, 1685, 1618, 1589, 1575, 1224 cm$^{-1}$; $^1$H NMR δ 8.36 (br s, 1 H), 7.36–7.27 (m, 5 H), 6.60 (bs s, 1 H), 6.10–6.00 (m, 1 H), 4.68–4.63 (m, 1 H), 4.53–4.47 (m, 2 H), 3.25 (s, 3 H), 3.25–3.11 (m, 2 H), 2.99–2.84 (m, 2 H), 2.71 (br, 2 H), 2.55 (dd, 1 H, J=19.5, 8.9 Hz), 2.38 (dd, 1 H, J=14.4, 7.6 Hz), 2.32–2.05 (m, 2 H), 2.05 (s, 3 H), 1.85 (br s, 1 H), 1.80 (dd, 1 H, J=14.5, 4.7 Hz), 1.52 (s, 3 H), 0.82 (s, 3 H); $^{13}$C NMR δ 217.3, 178.9, 169.9, 164.7, 158.3, 151.7, 138.8, 137.1, 134.9, 129.0 (3 C), 128.6, 128.1 (2 C), 88.7, 82.2, 73.4, 67.9, 64.3, 59.4, 49.1, 42.7, 42.5, 37.8 (2 C), 36.3, 25.2, 22.5, 21.1, 16.3; MS (EI) m/z (rel. intensity) 549 (M$^+$, 14), 489 (37), 415 (5), 120 (23), 91 (100); HRMS (EI) calculated for C$_{31}$H$_{35}$NO$_8$ 549.2363. found 549.2340.

For therapeutic treatment of the specified indications, a wortmannin analog of FIGS. 1–3 may be administered as such, or can be compounded and formulated into pharmaceutical compositions in unit dosage form for parenteral, transdermal, rectal, nasal, local intravenous administration, or, preferably, oral administration. Such pharmaceutical compositions are prepared in a manner well known in the art and comprise at least one active compound selected from the group consisting of those wortmannin analogs of FIGS. 1–3 associated with a pharmaceutically carrier. The term "active compound", as used throughout this specification, refers to at least one compound selected from compounds of the formulas or pharmaceutically acceptable salts thereof.

The term "effective amount" as used herein, means an amount of a compound of the present invention that is capable of inhibiting, blocking, or reversing the activation, migration, or proliferation of cells. The activity contemplated by the present methods includes both medical therapeutic and/or prophylactic treatment, as appropriate. The specific dose of a compound administered according to this invention to obtain therapeutic and/or prophylactic effects will, of course, be determined by the particular circumstances surrounding the case, including, for example, the compound administered, the route of administration, and the condition being treated.

The compounds are effective over a wide dosage range and, for example, dosages per day will normally fall within the range of from 0.001 to 10 mg/kg, more usually in the range of from 0.01 to 1 mg/kg. However, it will be understood that the effective amount administered will be determined by the physician in the light of the relevant circumstances including the condition to be treated, the choice of compound to be administered, and the chosen route of administration, and therefore the above dosage ranges are not intended to limit the scope of the invention in any way.

The term "inhibiting" includes the administration of a compound of the present invention to prevent the onset of the symptoms, alleviating the symptoms, or eliminating the disease, condition or disorder.

In such a composition, the active compound is known as "active ingredient". In making the compositions, the active ingredient will usually be mixed with a carrier, or diluted by a carrier, or enclosed within a carrier that may be in the form of a capsule, sachet, paper or other container. When the carrier serves as a diluent, it may be a solid, semisolid, or liquid material that acts as a vehicle, excipient of medium for the active ingredient. Thus, the composition can be in the form of tablets, pills, powders, lozenges, sachets, cachets, elixirs, emulsions, solutions, syrups, suspensions, soft and hard gelatin capsules, sterile injectable solutions, and sterile packaged powders.

Some examples of suitable carriers, excipients, and diluents include lactose, dextrose, sucrose, sorbitol, mannitol, starches, gum acacia, calcium phosphate alginates, calcium salicate, microcrystalline cellulose, polyvinylpyrrolidone, cellulose, tragacanth, gelatin, syrup, methyl cellulose, methyl- and propylhydroxybenzoates, talc, magnesium stearate, water, and mineral oil. The formulations can additionally include lubricating agents, wetting agents, emulsifying and suspending agents, preserving agents, sweetening agents or flavoring agents. The compositions may be formulated so as to provide quick, sustained, or delayed release of the active ingredient after administration to the patient by employing procedures well known in the art.

For oral administration, a compound can be admixed with carriers and diluents, molded into tablets, or enclosed in gelatin capsules. The mixtures can alternatively be dissolved in liquids such as 10% aqueous glucose solution, isotonic saline, sterile water, or the like, and administered intravenously or by injection.

By "pharmaceutically acceptable", it is meant the carrier, diluent or excipient must be compatible with the other ingredients of the formulation and not deleterious to the recipient thereof.

The local delivery of inhibitory amounts of active compound for the treatment of cancer can be by a variety of techniques that administer the compound at or near the proliferative site. Examples of local delivery techniques are not intended to be limiting but to be illustrative of the techniques available. Examples include local delivery catheters, site specific carriers, implants, direct injection, or direct applications. Local delivery by a catheter allows the administration of a pharmaceutical agent directly to the proliferative site.

Local delivery by an implant describes the surgical placement of a matrix that contains the pharmaceutical agent into the proliferative lesion. The implanted matrix releases the pharmaceutical agent by diffusion, chemical reaction, or solvent activators.

Another example is the delivery of a pharmaceutical agent by polymeric endoluminal sealing. This technique uses a catheter to apply a polymeric implant to the interior surface of the lumen. The pharmaceutical agent incorporated into the biodegradable polymer implant is thereby released at the surgical site. It is described in PCT WO 90/01969 (Schindler, Aug. 23, 1989).

A final example of local delivery by an implant is by direct injection of vesicles or microparticulates into the proliferative site. These microparticulates may be composed of substances such as proteins, lipids, carbohydrates or synthetic polymers. These microparticulates have the pharmaceutical agent incorporated throughout the microparticle or over the microparticle as a coating. Delivery systems incorporating microparticulates are described in Lange, Science 249: 1527–1533 (September, 1990) and Mathiowitz, et al., J. App. Poly. Sci., 26:809 (1981).

Local delivery by site specific carriers describes attaching the pharmaceutical agent to a carrier which will direct the drug to the proliferative lesion. Examples of this delivery technique include the use of carriers such as a protein ligand or a monoclonal antibody.

Local delivery by direct application includes the use of topical applications. An example of a local delivery by direct application is applying the pharmaceutical agent to the arterial tumor or area left behind after resection of the tumor.

Formulation of wortmannin analogs is well known in the art as is the fermentation process. Rather than get into exhaustive detail regarding synthetic scheme or formulation, the present invention relies on the skilled artisan to use those common synthetic and formulation techniques to synthesize compounds of the following general formula:

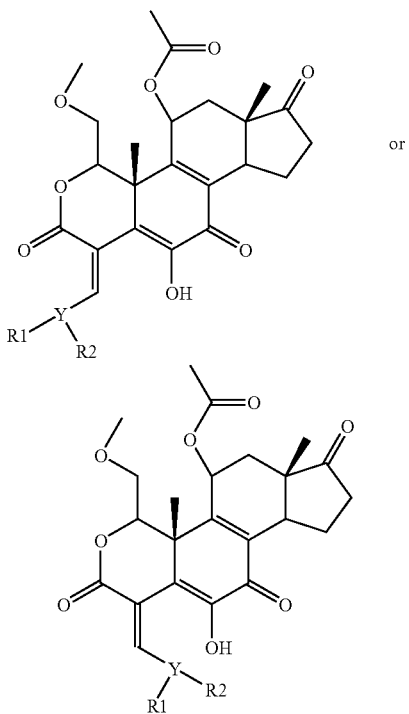

Wherein Y is a heteroatom and R1 or R2 are unsaturated alkyl, non-linear alky, branched alky, substituted alkyl or cyclic alkyl. Preferably, the present invention has a chemical formula corresponding to those shown in FIGS. 1–3. Even more preferably, the present invention has a chemical formula in accordance with those shown in FIG. 2.

The proliferation of cells is dependent on the PI 3-kinase-AKT-mTOR signaling pathway. In addition signaling through PI 3-kinase and AKT appears to inhibit apoptosis.

The following Table I illustrates the Activity and in vivo toxicity of the wortmannin analogues Enzyme inhibition The ability of wortmannin and the analogues to inhibit phosphatidylinositol-3-kinase and mTOR is expressed as the dose to cause 50% inhibition ($IC_{50}$). Cytotoxicity-Growth inhibition of human MCF-7 breast cancer cells was measured over 4 days using the MTT assay expressed as the dose to cause 50% inhibition ($IC_{50}$). Toxicity—Groups of 3 C57BL6 mice were administered wortmannin at doses of 1, 2 or 3 mg/kg or the analogues at 1, 3, 9 or 18 mg/kg where sufficient compound was available by the intraperitoneal route daily for 4 days. The animals were killed 24 hr after the last dose and differential blood counts and serum chemistry determined. The major toxicities observed were liver toxicity and lymphocytopenia with decreased red blood cell counts and increased serum glucose at higher doses. Toxicities are measured at the maximum tolerated dose or the highest dose tested Liver toxicity is measured as the mean percent increase in serum ALT and AST expressed relative to wortmannin as 1.0. Lymphocytopenia is expressed as the percent decrease in lymphocyte counts relative to wortmannin as 1.0. A low liver toxicity and a high lymphocyte toxicity as a surrogate for inhibition of tumor cell growth is the desirable feature. Highlighted are the compounds being made for antitumor testing.

Based on the above evidence, it would appear that an inhibitor of PI 3-kinase will inhibit cell growth and survival. Moreover, PI 3-kinase inhibitors should also inhibit the local inflammatory response, especially in the case of a bioprosthetic implant, which could be favorable factor for long-term engraftment or other bioprosthetic implant. In principle, the wortmannin derivatives could be ideal agents for inducing a temporary block of the PI 3-kinase-AKT-mTOR pathway.

FIG. 4–9 illustrate the effect of Wortmannin and Analogs (See FIG. 2) Against PC-3 Human Prostate Cancer; against HT-29 Human Colon Cancer; against OVCAR-3 Human Ovarian Tumor; on Weight Loss; and anti-tumor activity.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

TABLE I

| Compound | NSC # | Maximum tolerated dose[e] mg/kg ip qD × 4 | PI-3 kinase inhibition $IC_{50}$ (nM) | mTOR inhibition $IC_{50}$ (µM) | cytotoxicity NCI cell panel $IC_{50}$ (µM) | Lymphocyte toxicity relative to wortmannin[b] | Liver toxicity relative to wortmannic[b] | Ratio liver toxicity/ lymphocyte toxicity[d] |
|---|---|---|---|---|---|---|---|---|
| wortmannin | 221019 | 2.5 | 0.3 | 0.1 | 8.9 | 1.0 | 1.0 | 1.0 |
| DJM2-166 | 722134 | 20[f] | 0.5 | >3 | 2.2 | 2.2 | 0.3 | 0.1 |
| DJM2-167 | 722135 | 20 | 1.1 | >3 | 0.5 | 2.4 | 0.3 | 0.1 |
| DJM2-168 | 722136 | >20 | 0.1 | >3 | 11.9 | 0.6 | 0.1 | 0.2 |
| DJM2-170 | 722137 | 9 | 1.0 | >3 | 7.1 | 1.1 | 1.7 | 1.5 |
| DJM2-171 | 722138 | 6 | 0.1 | >3 | 10.2 | 0.7 | 1.1 | 1.6 |
| DJM2-177 | 722142 | 6 | 0.3 | 1.5 | 10.2 | 2.0 | 0.2 | 0.1 |
| DJM2-180 | 722139 | >30 | 10 | 2.0 | 8.1 | 0.5 | 0.3 | 0.6 |
| DJM2-181 | 722140 | >18 | 0.1 | >3 | 0.7 | 1.9 | 0.2 | 0.1 |
| DJM2-182 | 722141 | >18 | 0.4 | >3 | 1.0 | 0.8 | 0.1 | 0.1 |
| DJM2-186 | 722143 | >9 | ND | >3 | 27.7 | 0 | 0.4 | > |
| DJM2-189 | 722144 | >30 | 5 | >3 | 21.0 | 0 | 0.4 | > |
| DJM2-190 | 722145 | NE | 10 | >3 | 33.0 | 0.6 | NE | NE |

ND = not determined, NE = non evaluable insufficient drug
[a] 2 day MTT assay, mean of 60 cell lines
[b] lymphocyte toxicity at the MTD or highest dose tested expressed relative to wortmannin
[c] liver toxicity measured by the % ALT and AST at the MTD or highest dose tested expressed relative to wortmannin
[d] liver toxicity measured relative to wortmannin/decrease in blood lymphocytes relative to wortmannin
[e] MTD >10% body weight loss
[f] estimated value

We claim:
1. A compound of the formula:

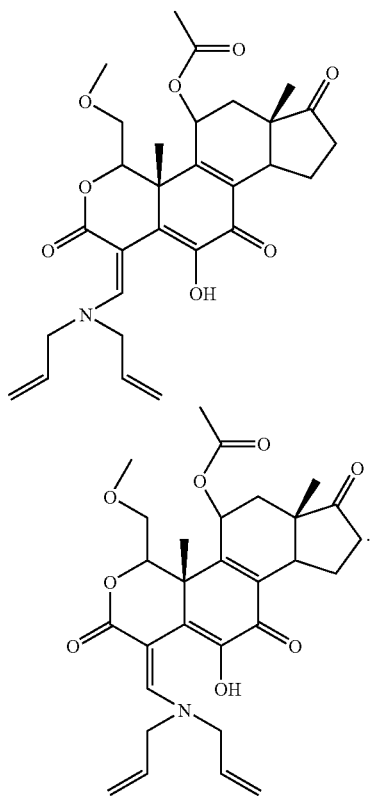

or

2. A compound of the formula:

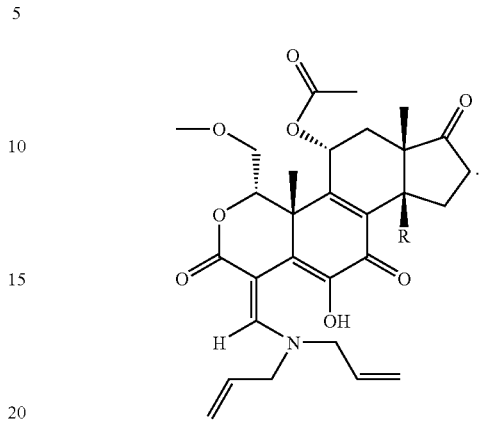

3. A pharmaceutical formulation comprising an effective amount of the compound of claim 1, and a pharmaceutically acceptable carrier, diluent, or excipient thereof.

4. A pharmaceutical formulation comprising an effective amount of the compound of claim 2, and a pharmaceutically acceptable carrier, diluent, or excipient thereof.

* * * * *

UNITED STATES PATENT AND TRADEMARK OFFICE
CERTIFICATE OF CORRECTION

PATENT NO. : 7,081,475 B2 Page 1 of 1
APPLICATION NO. : 10/245779
DATED : July 25, 2006
INVENTOR(S) : Powis et al.

It is certified that error appears in the above-identified patent and that said Letters Patent is hereby corrected as shown below:

Title page, item [75] inventor:
Wipf Peter should read: Peter Wipf

Signed and Sealed this

Thirtieth Day of January, 2007

JON W. DUDAS
*Director of the United States Patent and Trademark Office*

UNITED STATES PATENT AND TRADEMARK OFFICE
CERTIFICATE OF CORRECTION

PATENT NO.         : 7,081,475 B2                                              Page 1 of 1
APPLICATION NO. : 10/245779
DATED              : July 25, 2006
INVENTOR(S)        : Powis et al.

It is certified that error appears in the above-identified patent and that said Letters Patent is hereby corrected as shown below:

Title page, item [73]

Assignee: Prolx Pharmaceuticals Corp., Tuscon, AZ (US); Arizona Board of Regents, Acting on behalf of the University of Arizona, Tuscon, AZ (US); University of Pittsburgh, Pittsburgh, PA (US) should read:

Arizona Board of Regents, Acting on behalf of the University of Arizona, Tucson, AZ (US); University of Pittsburgh, Pittsburgh, PA (US)

Signed and Sealed this

Twenty-ninth Day of May, 2007

JON W. DUDAS
*Director of the United States Patent and Trademark Office*

UNITED STATES PATENT AND TRADEMARK OFFICE
CERTIFICATE OF CORRECTION

PATENT NO. : 7,081,475 B2 Page 1 of 1
APPLICATION NO. : 10/245779
DATED : July 25, 2006
INVENTOR(S) : Powis et al.

It is certified that error appears in the above-identified patent and that said Letters Patent is hereby corrected as shown below:

Delete Claim 2, col. 10 line 5-20 and insert:
-- 2. A compound of the formula:

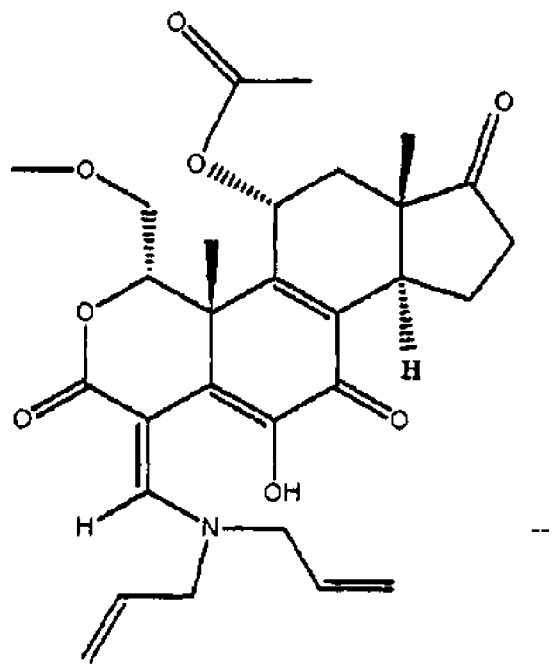

--

Signed and Sealed this

Twenty-sixth Day of May, 2009

JOHN DOLL
*Acting Director of the United States Patent and Trademark Office*